United States Patent
Hofmann et al.

(10) Patent No.: US 9,896,391 B2
(45) Date of Patent: Feb. 20, 2018

(54) PROCESS FOR PREPARING LINEAR α-OLEFINS

(75) Inventors: Karl Heinz Hofmann, Germering (DE); Hans Jorg Zander, Munich (DE); Anton Wellenhofer, Hohenschaftlarn (DE); Wolfgang Muller, Munich (DE); Anina Wohl, Munich (DE)

(73) Assignee: LINDE AKTIENGESELLSCHAFT, Munich (DE)

(*) Notice: Subject to any disclaimer, the term of this patent is extended or adjusted under 35 U.S.C. 154(b) by 446 days.

(21) Appl. No.: 13/576,414

(22) PCT Filed: Jan. 13, 2011

(86) PCT No.: PCT/EP2011/000131
§ 371 (c)(1),
(2), (4) Date: Sep. 13, 2012

(87) PCT Pub. No.: WO2011/095273
PCT Pub. Date: Aug. 11, 2011

(65) Prior Publication Data
US 2012/0330078 A1    Dec. 27, 2012

(30) Foreign Application Priority Data
Feb. 2, 2010 (DE) .................. 10 2010 006 589

(51) Int. Cl.
*C07C 2/08*    (2006.01)
(52) U.S. Cl.
CPC ..................... *C07C 2/08* (2013.01)
(58) Field of Classification Search
CPC .... C07C 2/08; C07C 2/22; C07C 2/32; C07C 2/34; C07C 11/02; C07C 2521/06; C07C 2531/02; C07C 2531/16
(Continued)

(56) References Cited

U.S. PATENT DOCUMENTS 3,349,148 A    10/1967   Bush
3,637,897 A    1/1972    Cull et al.
(Continued)

FOREIGN PATENT DOCUMENTS

DE    4338 414 C1    3/1995
DE    4338414 C1 *   3/1995
(Continued)

OTHER PUBLICATIONS

Walas, ("Chemical Reactors" in Perry's Chemical Engineer's Handbook, 7th ed., McGraw-Hill, 1997, R. H. Perry and D. W. Green, eds., pp. 23-44 to 23-49—available on-line Mar. 2001.*
(Continued)

*Primary Examiner* — In Suk Bullock
*Assistant Examiner* — Ali Z Fadhel
(74) *Attorney, Agent, or Firm* — Millen White Zelano & Branigan, PC

(57) ABSTRACT

The invention relates to a process for preparing linear α-olefins, wherein ethylene 1a is conducted into the oligomerization reactor 2 in the liquid phase. The oligomerization reactor 2 has a mechanical stirrer 2a in order to ensure optimal mixing of the liquid ethylene and of the catalyst in the liquid phase. From the top of the oligomerization reactor 2, vaporized ethylene is drawn off together with light α-olefins and a small proportion of the organic solvent. The gas mixture drawn off from the top of the reactor 2 is condensed together with gaseous fresh ethylene 7 by means of heat exchanger 3 and separator 4. The liquid phase drawn off from the separator 4 is conducted by means of circulation pump 5a as liquid ethylene input 1a back into the oligomerization reactor 2. The liquid products of the oligomerization reaction are drawn off 8 laterally from the base of the reactor 2.

12 Claims, 3 Drawing Sheets

Figure 1:
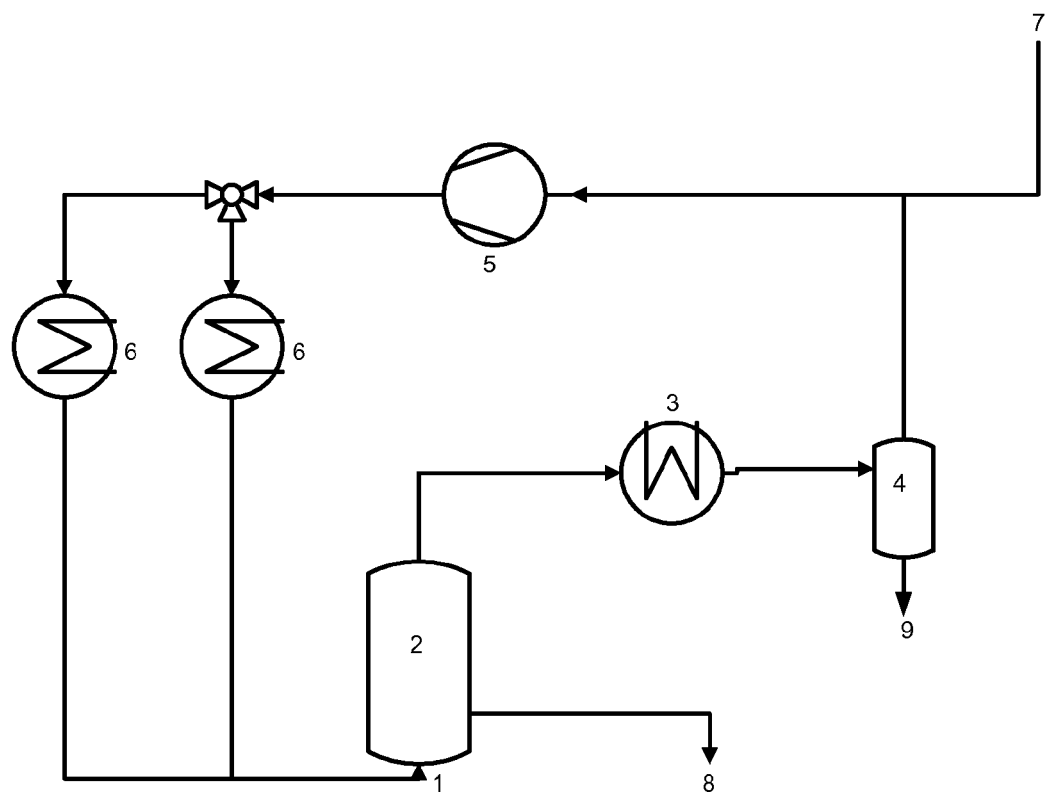

(58) Field of Classification Search
USPC ....... 585/501, 502, 510, 511, 512, 520, 521, 585/523
See application file for complete search history.

(56) References Cited

U.S. PATENT DOCUMENTS

| | | | |
|---|---|---|---|
| 3,655,812 A | | 4/1972 | Langer, Jr. |
| 3,862,257 A | * | 1/1975 | Buben et al. .................. 585/523 |
| 4,020,121 A | * | 4/1977 | Kister ....................... C07C 2/08 585/504 |
| 4,040,121 A | | 8/1977 | Grundy |
| 4,155,946 A | | 5/1979 | Sato et al. |
| 5,557,023 A | * | 9/1996 | Somogyvari et al. ........ 585/513 |
| 5,962,761 A | * | 10/1999 | Sechrist ..................... C07C 2/32 203/49 |
| 6,534,691 B2 | | 3/2003 | Culver et al. |
| 2002/0016521 A1 | | 2/2002 | Culver et al. |
| 2003/0153798 A1 | | 8/2003 | Kobayashi et al. |
| 2004/0122271 A1 | | 6/2004 | Van Zon et al. |
| 2004/0192803 A1 | * | 9/2004 | Figovsky et al. ............. 521/178 |
| 2009/0203946 A1 | | 8/2009 | Chuang |
| 2009/0216057 A1 | * | 8/2009 | Fritz ........................ C07C 2/30 585/532 |
| 2009/0306312 A1 | | 12/2009 | Fritz et al. |
| 2010/0249343 A1 | | 9/2010 | Kleingeld et al. |
| 2010/0268006 A1 | | 10/2010 | Gildenhuys |

FOREIGN PATENT DOCUMENTS

| | | | | |
|---|---|---|---|---|
| EP | 1 748 038 A1 | | 1/2007 | |
| EP | 1 749 806 A1 | | 2/2007 | |
| FR | 1419732 A | | 12/1965 | |
| JP | 50-7043 A | | 3/1975 | |
| JP | 54-12303 A | | 1/1979 | |
| JP | 2001-89399 A | | 4/2001 | |
| JP | 2002-255863 A | | 9/2002 | |
| JP | 2004-504282 A | | 2/2004 | |
| JP | 2006-500412 A | | 1/2006 | |
| RU | 2111200 C1 | | 5/1998 | |
| SU | 1211249 A1 | | 2/1986 | |
| WO | WO03/053890 | * | 7/2003 | ............... C07C 2/32 |
| WO | WO 03053890 A1 | * | 7/2003 | |
| WO | 2009/060342 A2 | | 5/2009 | |
| WO | 2009/060343 A1 | | 5/2009 | |
| WO | WO 2009/060342 A2 | | 5/2009 | |
| WO | WO 2009/060343 A1 | | 5/2009 | |
| WO | WO2009/060343 A1 | * | 5/2009 | ............... C07C 2/36 |
| WO | WO 2009060343 A1 | * | 5/2009 | |

OTHER PUBLICATIONS

Seider et al., "Product and Process Design Principles, Synthesis, Analysis and Evaluation", Second Edition, 2004, p. 514-515 and 520-521.*
International Search Report of PCT/EP2011/000131 (dated Jul. 28, 2011).
English Translation Abstract of JP 2001-089399 published Apr. 3, 2001.
English Translation Abstract of JP 2002-255863 published Sep. 11, 2002.
English language translation of Decision on Grant for corresponding Russian Patent Application No. 2012137219/04(060376); dated Mar. 11, 2015.
English language Abstract for Russian Patent Application No. 2111200; published May 20, 1998.
Thomson Innovation Patent Record View for SU 1211249, published Feb. 15, 1986.
European Opposition dated Aug. 10, 2016 for corresponding European Application No. 11700391.3.
English language Abstract for German Application No. DE4338414C1; published Mar. 16, 1995.

* cited by examiner

*State of the art*

PROCESS FOR PREPARING LINEAR α-OLEFINS

The invention relates to a process for preparing linear α-olefins by oligomerizing ethylene in the presence of an organic solvent and of a homogeneous liquid catalyst in a reactor.

A process of this type for preparing linear α-olefins by oligomerization of ethylene is disclosed, for example, in DE 4338414. According to the prior art, the oligomerization takes place in the liquid phase in the lower section of an oligomerization reactor. Since the reaction is exothermic and too high a reaction temperature would lead to a deterioration in the product quality, the heat of reaction has to be removed. According to the prior art, this is accomplished by a cooling circuit by means of direct cooling and gaseous ethylene as a coolant. Gaseous ethylene from the ethylene circuit is conducted into the reactor and dissolved in the liquid phase. This maintains the ethylene concentration required for the oligomerization reaction. The excess of ethylene is used to control the reaction temperature. Since the reaction is strongly exothermic, a large amount of gaseous ethylene is needed for the removal of the heat of reaction, i.e. for direct cooling of the reaction. Only a small amount of the ethylene used reacts in the actual oligomerization reaction.

The prior art will now be explained in detail with reference to FIG. 1. The gaseous ethylene 1 is supplied to the base region of the oligomerization reactor 2. In the reactor 2 is an organic solvent with a homogeneous liquid catalyst. The gaseous ethylene 1 passes through the solvent containing the liquid catalyst, which oligomerizes a small portion of the gaseous ethylene to linear α-olefins. Near the top of the oligomerization reactor 2, a mixture of the majority of the ethylene, light α-olefins and, according to the thermodynamic equilibrium in the reactor, some organic solvent leaves the reactor. This gas mixture is cooled in the cooler 3 and transferred into the separator 4. The liquid phase 9 which forms in the course of cooling consists principally of solvent and light α-olefins, and is drawn off from the bottom of the separator 4 and conducted into the reactor or to further separation (not shown). The majority of the gaseous ethylene leaves the separator 4 via the top and is conducted together with fresh ethylene 7 into a circulation compressor 5. In the downstream heat exchangers 6, the gaseous ethylene is warmed back to the input temperature, for example 10° C., and conducted as a feedstock back into the oligomerization reactor 2. In order to regulate the input temperature of the gaseous ethylene, two heat exchangers 6 are needed here. The two heat exchangers 6 are regulated to constant and different temperatures. The input temperature of the gaseous ethylene is regulated by the relative proportions from the two heat exchangers 6, the total amount of gaseous ethylene as the input into the reactor being kept constant. A variable input temperature of the gaseous ethylene 1 is needed to keep the reaction temperature constant even in the case of varying conversions and hence varying release of heat. The actual product 8 of the oligomerization reaction is drawn off laterally from the oligomerization reactor 2 together with solvent. The liquid mixture 8 drawn off is subsequently separated into solvent containing liquid catalyst and the linear α-olefin product. The solvent containing liquid catalyst is regenerated and recycled into the oligomerization reactor (not shown). The linear α-olefins are separated into the individual α-olefins (not shown).

Alternatively, the temperature of the gaseous ethylene 1 which is conducted into the reactor 2 as an input can be regulated with a heat exchanger 6. In this case, however, the temperature of the heat exchanger 6 must be variable.

The process outlined according to the prior art has a series of disadvantages. In order to remove the heat of reaction of the oligomerization reactor, a large amount of gaseous ethylene has to be circulated. Correspondingly, the dimensions of the circulation compressor have to be very large. Secondly, the control of the reaction temperature via the input temperature of the gaseous ethylene with the two heat exchangers or one regulable heat exchanger is inconvenient and complicated.

To avoid these disadvantages, EP 1 748 038 proposes using, as a feedstock for the oligomerization reactor, a small amount of gaseous ethylene and a large amount of inert gas. The inert gases proposed here are principally hydrocarbons such as methane, ethane, propane and propylene, and also hydrogen. Here too, it is necessary to circulate a large amount of gas.

EP 1 749 806 discloses a process for preparing linear α-olefins by oligomerizing ethylene, in which the top of the reactor is cooled by means of a coolant, with the temperature in the top of the reactor kept at 15 to 20° C. and cooling by means of a condenser, the coolant used being propylene. In this case, propylene is liquefied at the top of the reactor and vaporized in the base region of the reactor. This process has the disadvantage that an increased extent of deposit formation occurs on the cold surfaces of the condenser, for example as a result of polymers introduced.

The present invention is based on the problem of alternatively configuring a process for preparing linear α-olefins by oligomerizing ethylene.

A further problem addressed by the present invention is that of reducing the amount of ethylene in the circuit.

In addition, deposit formation in the plant parts is to be reduced.

The present problems are solved by the features of claim 1. Further advantageous configurations of the invention are specified in the dependent claims.

According to the invention, the ethylene is introduced into the reactor at least partly in the liquid state. This significantly increases the capacity to absorb heat of the ethylene introduced. In the case of introduction of the ethylene in the liquid state, the ethylene can absorb much more heat which arises in the oligomerization reaction. The heat absorption capacity of the oligomerization reaction is increased by the amount of heat of vaporization. It is thus possible to absorb the same amount of heat of the oligomerization reaction by means of a significantly smaller amount of ethylene. This allows the amount in the ethylene circuit to be reduced significantly compared to the prior art, and the temperature regulation of the oligomerization reaction to be simplified significantly. By virtue of the small amount circulated, deposit formation is also reduced in the particular plant parts, since a significantly smaller amount of potential deposit formers is also circulated. By virtue of the significantly smaller amount of ethylene which is circulated, the probability of entrained droplets from the biphasic layer of the reactor is also minimized. As a result, a significantly lower level of potential deposit formers passes from the reactor into the circuit. In addition, supply in the liquid phase allows good mixing of the ethylene with the catalyst material present in the liquid phase. Therefore, the oligomerization reaction proceeds with unreduced yield.

In an advantageous configuration of the invention, a liquefied inert gas is additionally introduced into the reactor. An inert gas is understood in the context of the application to mean any gas which behaves inertly with regard to the reactions which take place in the reactor. The liquefied inert gases used are preferably hydrocarbons, preferably propylene, propane and/or hydrocarbons having four carbon atoms. In this configuration of the invention, in addition to ethylene, a liquefied inert gas is introduced into the reaction as a coolant. The liquefied inert gas evaporates in the reactor and is condensed again together with the vaporized ethylene, and recycled into the reactor as a feedstock. The liquefied inert gas selected is readily vaporizable and condensable at acceptable temperatures. The inert gases mentioned here are a good compromise between easy vaporizability under reaction conditions and condensability at coolant temperature. In addition, it has been found that, surprisingly, ethylene can be condensed significantly more easily together with the inert gases mentioned than ethylene alone. The energy expenditure for the liquefaction therefore falls further in this configuration of the invention.

In one configuration of the invention, the reactor has a mechanical stirrer, preferably a gas-introducing stirrer, more preferably a hollow-shaft introducing stirrer. The mechanical stirrer significantly improves the mixing of the gas phase, the liquid phase and the liquid catalyst material. In the case of supply of ethylene via the mechanical stirrer, no further internals are required, and the mixing becomes significantly more efficient. Particularly the use of a hollow-shaft introducing stirrer is appropriate. The hollow-shaft introducing stirrer sucks in the gas phase of the reactor, which further improves the mixing in the reactor.

In a further configuration of the invention, the ethylene, or ethylene and inert gas, which leaves the reactor in gaseous form is only partly condensed. In this configuration of the invention, the dimensions of the condensation are such that the complete gas stream from the reactor is not condensed. The result is a biphasic mixture. The biphasic mixture is separated in a separator, and the liquid phase composed of ethylene or ethylene and inert gas is recycled directly into the reactor, while the gas phase, after compression, is recycled in gaseous form into the reactor. In this configuration of the invention too, the apparatus complexity of the compression is reduced significantly compared to the prior art. In addition, the additional supply in the gas phase leads to better mixing of the reactor contents compared to recycling of a pure liquid phase. On entry into the reactor, the gas displaces the liquid phase, and the resulting bubble formation increases turbulence and hence mixing in the reactor.

Advantageously, the temperature regulation of the reactor is controlled by the control of the volume flow of the liquid phase supplied. In the case of use of a circuit with a liquid coolant, i.e. with ethylene in the liquid phase or ethylene and an inert gas in the liquid phase, the reaction temperature in the oligomerization reactor can be regulated by the control of the volume flow of the input of liquid coolant. Temperature regulation by the control of the volume flow is much simpler than regulation of the input temperature. It is therefore possible in this configuration of the invention to dispense with the one heat exchanger for regulation of the input temperature according to the prior art.

It is possible with the present invention, more particularly, to significantly reduce the apparatus complexity in the performance of a process for preparing linear α-olefins by oligomerization of ethylene. The supply of ethylene in the liquid phase into the oligomerization reactor significantly reduces the amount of coolant required. This allows the circulation compressor for the cooling circuit to be designed for a much smaller amount and to be replaced by a simple circulation pump. In addition, in the case of supply of ethylene in the liquid phase, a heat exchanger for regulation of the input temperature is omitted, or the regulation of the inlet temperature of the ethylene is simplified significantly. This significantly reduces the capital costs of such a process compared to the prior art. In addition, a lower level of deposit formers is circulated, and so the risk of deposit formation and the associated cleaning operations are reduced. The present invention forms an alternative process to the prior art for preparation of linear α-olefins by oligomerizing ethylene.

The invention will be illustrated in detail hereinafter by a comparison of a working example of the invention with the prior art.

Figure 2:
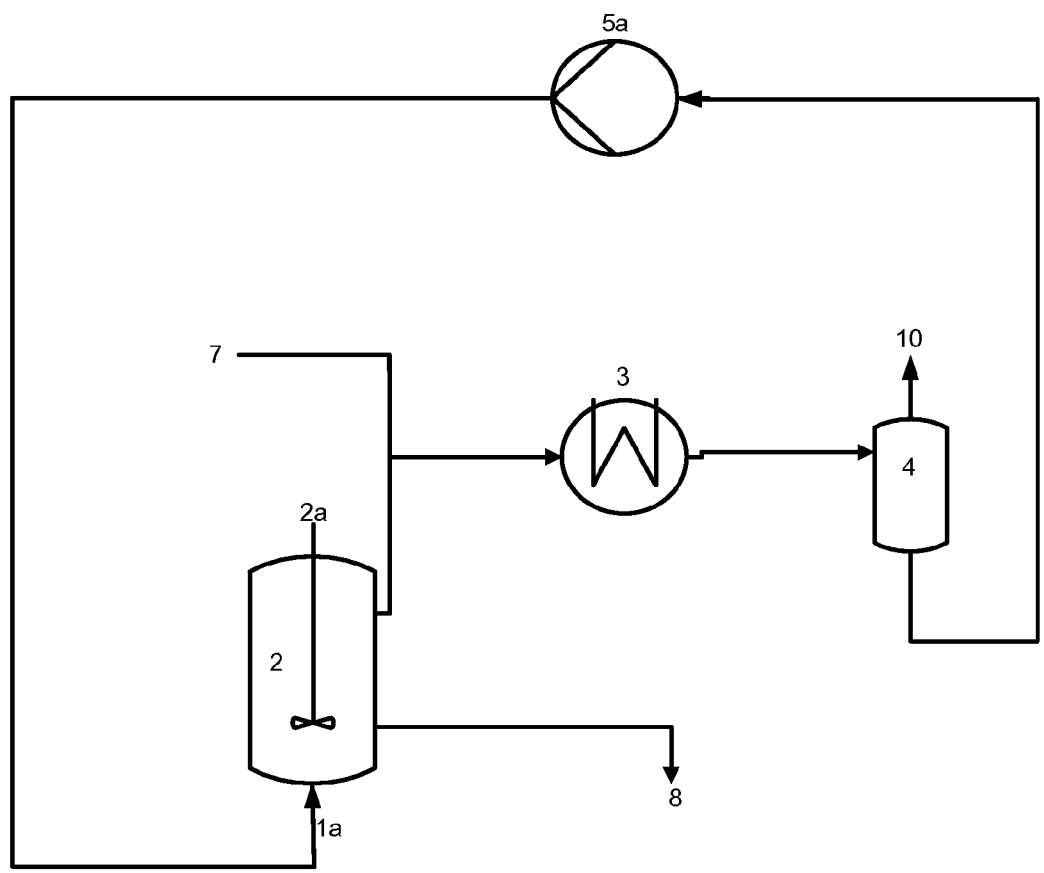
Figure 3:
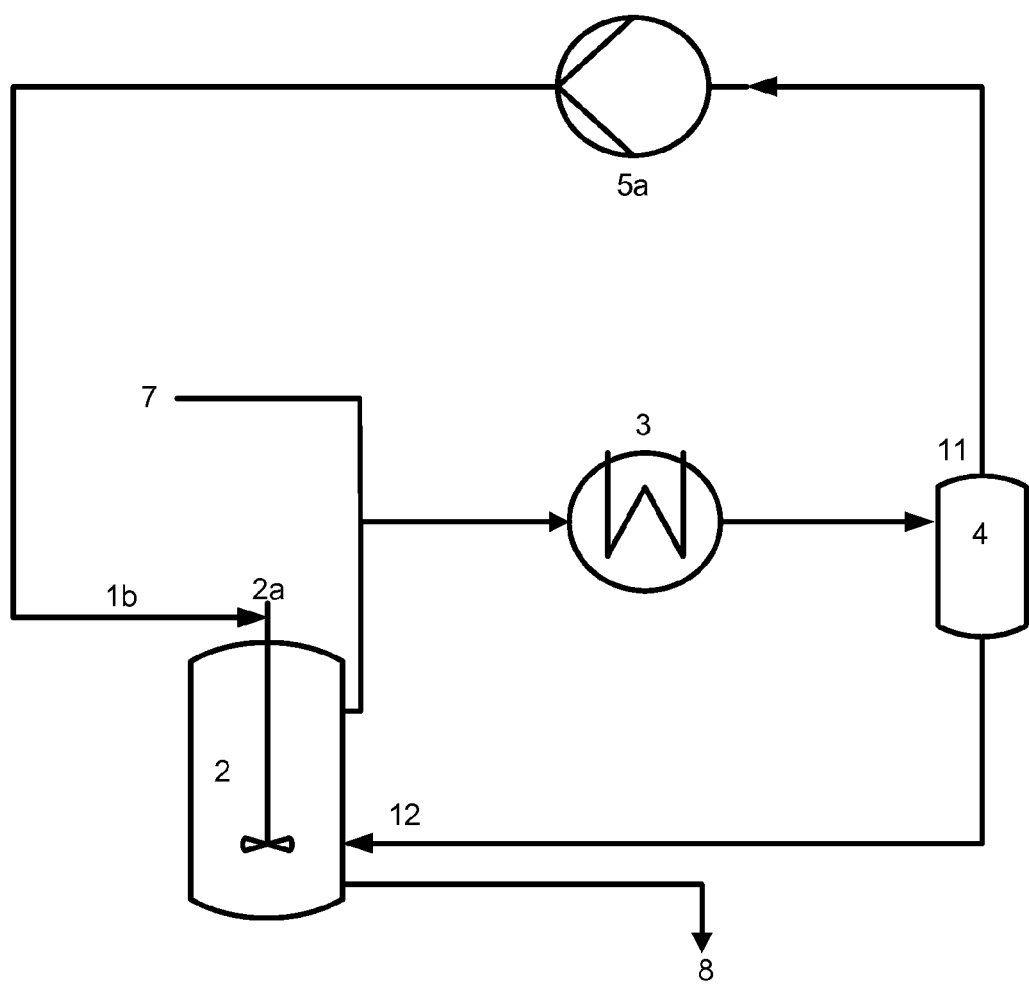

The figures show:

FIG. 1 a process for preparing linear α-olefins by means of oligomerization according to the prior art FIG. 2 one configuration of the invention FIG. 3 a further configuration of the invention FIG. 1 shows a process for preparing linear α-olefins according to the prior art. The prior art process shown in FIG. 1 uses ethylene 1 in the gaseous phase and has already been explained in the introductory part of the description.

FIG. 2 shows one configuration of the invention, in which ethylene 1a is conducted in the liquid phase into the oligomerization reactor 2. The oligomerization reactor 2 has a mechanical stirrer 2a in order to ensure optimal mixing of the liquid ethylene and of the catalyst in the liquid phase. From the top of oligomerization reactor 2, vaporized ethylene is drawn off together with light α-olefins and a small proportion of the organic solvent. The gas mixture drawn off from the top of the reactor 2 is condensed together with gaseous fresh ethylene 7 by means of heat exchanger 3 and separator 4. The liquid phase drawn off from the separator 4 is conducted back into the oligomerization reactor 2 as liquid ethylene input 1a by means of circulation pump 5a. If the condensation of the ethylene is incomplete, the excess gas phase 10 is drawn off from the top of the separator. The separator 4 ensures that no biphasic mixture gets into the circulation pump 5a. The liquid products of the oligomerization reaction are drawn off 8 laterally from the base of the reactor 2.

The amount of ethylene in the cooling circuit has been reduced significantly compared to the prior art shown in FIG. 1. In both cases, the oligomerization reaction was performed experimentally at a pressure of approx. 30 bar and a temperature of approx. 60° C. In both cases, 10 tonnes per hour of liquid product 8 were drawn off and, correspondingly, 10 tonnes per hour of gaseous fresh ethylene 7 were added. In the prior art, 200 tonnes per hour of ethylene are circulated for cooling by means of the circulation compressor. This corresponds to an amount of ethylene of 5000 cubic meters per hour. According to the working example of the invention shown in FIG. 2, only 47 tonnes per hour of ethylene are circulated in the cooling circuit. This corresponds to 120 cubic meters per hour of ethylene in the liquid phase. This allows a simple circulation pump 5a to be used, in contrast to the circulation compressor 5 according to the prior art. The two heat exchangers 6 according to the prior art are dispensed with completely in this working example. The input temperature of the reactor is controlled by the regulation of the volume flow of the liquid ethylene 1a.

FIG. 3 shows a further configuration of the invention. In this configuration of the invention, the ethylene which leaves the reactor in gaseous form is not completely condensed in the heat exchanger 3. The biphasic mixture formed is separated in the separator 4. The gaseous phase 11 is compressed and recycled in gaseous form into the reactor 2. At the same time, the gaseous ethylene 1b is introduced into the reactor 2 via a hollow-shaft gas-introducing stirrer 2a. The liquid phase 12 from the separator 4 is recycled directly into the reactor 2.

The invention claimed is:
1. A process for preparing linear α-olefins comprising:
introducing ethylene into a reactor in a liquid state,
oligomerizing said ethylene in the presence of an organic solvent and a homogeneous liquid catalyst resulting in linear α-olefins,
recovering from the reactor a liquid product stream comprising the linear α-olefins and a gaseous stream comprising ethylene,
partly condensing the gaseous stream to form a biphasic mixture,
separating in a separator the biphasic mixture to form a liquid phase and a gas phase,
recycling the liquid phase directly into the reactor,
compressing the gas phase, and
recycling the compressed gas phase into the reactor in gaseous form,
wherein the gas phase recycled to the reactor consists of the entire gas phase from the separator.

2. The process according to claim 1, wherein a liquefied inert gas is additionally introduced into the reactor.

3. The process according to claim 2, wherein the liquefied inert gas comprises hydrocarbons.

4. The process according to claim 3, wherein the hydrocarbons are propylene, propane and/or hydrocarbons having four carbon atoms.

5. The process according to claim 1, wherein the reactor has a gas-introducing mechanical stirrer.

6. The process according to claim 4, wherein the mechanical stirrer consist of a hollow-shaft introducing stirrer.

7. The process according to claim 1, wherein a temperature of the reactor is regulated by the control of the volume flow of the liquid phase recycled.

8. The process of claim 1, wherein the gas phase leaving the separator is recycled directly into the reactor only undergoing compression.

9. A process for preparing linear α-olefins comprising:
introducing ethylene into a reactor in a liquid state,
preparing linear α-olefins by oligomerizing the ethylene in the presence of an organic solvent and a homogeneous liquid catalyst in the reactor,
recovering from the reactor a liquid product stream comprising the linear α-olefins and a gaseous stream comprising ethylene,
partly condensing the gaseous stream to form a biphasic mixture,
separating said biphasic mixture in a separator to form a liquid phase and a gas phase,
recycling the liquid phase directly into the reactor,
compressing the gas phase, and
recycling the compressed gas phase into the reactor in gaseous form,
wherein the gas phase recycled to the reactor consists of the entire gas phase from the separator.

10. The process of claim 9, wherein the gas phase leaving the separator is recycled directly into the reactor only undergoing compression.

11. A process comprising:
introducing ethylene into a reactor in a liquid state,
oligomerizing said ethylene in the reactor in the presence of an organic solvent and a homogeneous liquid catalyst resulting in linear α-olefins,
recovering from the reactor a liquid product stream comprising the linear α-olefins and a gaseous stream comprising ethylene,
partly condensing the gaseous stream to form a biphasic mixture,
separating said biphasic mixture in a separator to form a liquid phase and a gas phase,
recycling the liquid phase directly into the reactor, and
compressing the gas phase and recycling the compressed gas phase into the reactor in gaseous form,
wherein the gas phase recycled to the reactor consists of the entire gas phase from the separator.

12. The process of claim 11, wherein the gas phase leaving the separator is recycled directly into the reactor only undergoing compression.

* * * * *